US008426384B2

(12) United States Patent
Conti et al.

(10) Patent No.: US 8,426,384 B2
(45) Date of Patent: *Apr. 23, 2013

(54) WOUND-HEALING PHARMACEUTICAL COMPOSITIONS IN THE FORM OF A STERILE POWDER BASED ON AMINO ACIDS AND SODIUM HYALURONATE

(75) Inventors: Franco Conti, Milan (IT); Francesco Saverio Dioguardi, Milan (IT); Edoardo Carlo Maria Conti, legal representative, Milan (IT); Federico Giovanni Maria Conti, legal representative, Milan (IT); Isabella Arborio Mella, legal representative, Milan (IT)

(73) Assignee: Professional Dietetics S.r.l., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 12/964,419

(22) Filed: Dec. 9, 2010

(65) Prior Publication Data

US 2011/0077218 A1    Mar. 31, 2011

Related U.S. Application Data

(63) Continuation of application No. 12/091,551, filed as application No. PCT/EP2006/009968 on Oct. 16, 2006, now abandoned.

(30) Foreign Application Priority Data

Oct. 26, 2005   (IT) .............................. MI2005A2037

(51) Int. Cl.
*A61K 31/715*   (2006.01)
*A61P 17/02*    (2006.01)

(52) U.S. Cl.
USPC ........................................................ 514/55

(58) Field of Classification Search .................. None
See application file for complete search history.

(56) References Cited

U.S. PATENT DOCUMENTS

| 6,645,948    | B2 * | 11/2003 | Petito et al. ............ 514/62 |
| 2002/0013359 | A1 * | 1/2002  | Dioguardi .............. 514/423 |
| 2003/0021834 | A1 * | 1/2003  | Petito .................. 424/445 |
| 2008/0261915 | A1   | 10/2008 | Conti |

FOREIGN PATENT DOCUMENTS

WO    WO03/013487    *   2/2003

OTHER PUBLICATIONS

Berge, S. M., Journal of Pharmaceutical Sciences, "Pharmaceutical Salts", 1977, vol. 66, No. 1, pp. 1-19.*
Eastoe, J. E., Biochemical Journal, "The Amino Acid Composition of Mammalian Collagen and Gelatin", Dec. 1955, vol. 61, No. 4, pp. 589-600.*

Kuchel, P. W. et al., Schaum's Outline of Theory and Problems of Biochemistry, Second Edition, McGraw-Hill, copyright 1998, "Chapter 3: Amino Acids and Peptides", pp. 53-56 and 63-65.*
Notice of Abandonment issued by USPTO for U.S. Appl. No. 12/091,551, filed Apr. 25, 2008 in the name of Franco Conti; mail date: Feb. 11, 2011.
Restriction Requirement issued by USPTO for U.S. Appl. No. 12/091,481, filed Apr. 24, 2008 in the name of Franco Conti; mail date: Dec. 30, 2009.
Non-Final Office Action issued by USPTO for U.S. Appl. No. 12/091,481, filed Apr. 24, 2008 in the name of Franco Conti; mail date: Jun. 16, 2010.
Notice of Abandonment issued by USPTO for U.S. Appl. No. 12/091,481, filed Apr. 24, 2008 in the name of Franco Conti; mail date: Mar. 1, 2011.
Restriction Requirement issued by USPTO for U.S. Appl. No. 12/954,840, filed Nov. 26, 2010 in the name of Franco Conti; mail date: Jan. 26, 2012.
Non-Final Office Action issued by USPTO for U.S. Appl. No. 12/954,840, filed Nov. 26, 2010 in the name of Franco Conti; mail date: Feb. 27, 2012.
Non-Final Office Action issued by USPTO for U.S. Appl. No. 12/091,462, filed Apr. 24, 2008 in the name of Franco Conti; mail date: May 28, 2010.
Notice of Abandonment issued by USPTO for U.S. Appl. No. 12/091,462, filed Apr. 24, 2008 in the name of Franco Conti; mail date: Feb. 23, 2011.
Restriction Requirement issued by USPTO for U.S. Appl. No. 12/964,522, filed Dec. 9, 2010 in the name of Franco Conti; mail date: Jul. 27, 2012.
Non-Final Office Action issued by USPTO for U.S. Appl. No. 12/964,522, filed Dec. 9, 2010 in the anem of Franco Conti; mail date: Sep. 13, 2012.
Ashcroft, G.S. et al., Topical Estrogen Accelerates Cutaneous Wound Healing in Aged Humans Associated with an Altered Inflammatory Response, American Journal of Pathology, Oct. 1999, vol. 155, No. 4, pp. 1137-1146.
Greenhalgh, D.G. et al., PDGF and FGF Stimulate Wound Healing in the Genetically Diabetic Mouse, American Journal of Pathology, Jun. 1990, vol. 136, No. 6, pp. 1235-1246.
Ashcroft, G.S. et al., Mice lacking Smad3 show accelerated would healing and an impaired local inflammatory response, Nature Cell Biology, Sep. 1999, vol. 1, pp. 260-266.
El Ghalbzouri, A. et al., Fibroblasts facilitate re-epithelialization in wounded human skin equivalents, Laboratory investigation, 2004, vol. 84, 11 pages total.
Di Colandrea, T. et al., Epidermal Expression of Collagenase Delays Wound-Healing in Transgenic Mice, The Society for Investigative Dermatology, Inc., 1998, pp. 1029-1033.
Kapoor, M. et al., GSK-3β in mouse fibroblasts controls wound healing and fibrosis through an endothelin-1-dependent mechanism, The Journal of Clinical Investigation, Oct. 2008, vol. 118, No. 10, pp. 3279-3290.
Hu, C. et al., Basic fibroblast growth factor stimulates epithelial cell growth and epithelial wound healing in canine corneas, Veterinary Ophthalmology, 2009, vol. 12, No. 3, pp. 170-175.
Unemori, E.N. et al., Interleukin-1 and transforming growth factor-alpha: synergistic stimulation of metalloproteinases, PGE2, and proliferation in human fibroblasts, Exp. Cell Res., Feb. 1994, vol. 210, No. 2, 1 page total.

(Continued)

*Primary Examiner* — Layla Bland
*Assistant Examiner* — Bahar Craigo
(74) *Attorney, Agent, or Firm* — Steinfl & Bruno, LLP

(57) ABSTRACT

This invention relates to wound-healing pharmaceutical compositions in the form of a sterile powder based on amino acids and sodium hyaluronate.

8 Claims, No Drawings

OTHER PUBLICATIONS

Brown, R.L. et al., PDGF and TGF-α Act Synergistically to Improve Wound Healing in the Genetically Diabetic Mouse, Journal of Surgical Research, 1994, vol. 56, pp. 562-570.

Lee, P.-Y. et al., Electroporatic Delivery of TGF-β1 Gene Works Synergistically with Electric Therapy to Enhance Diabetic Wound Healing in db/db Mice, The Society for Investigative Dermatology, Inc., *J. Invest Dermatol*. 2004, 123, 791-798.

Cattaneo MG, Cappellini E, Benfante R, Ragni M, Omodeo-Salè F, Nisoli E, Borgese N, Vicentini LM Chronic deficiency of nitric oxide affects hypoxia inducible factor-1α (HIF-1α) stability and migration in human endothelial cells. *PLoS One*. 2011; 6(12):e29680. Epub Dec. 27, 2011.

Valerio A, Bertolotti P, Delbarba A, Perego C, Dossena M, Ragni M, Spano P, Carruba MO, De Simoni MG, Nisoli E. Glycogen synthase kinase-3 inhibition reduces ischemic cerebral damage, restores impaired mitochondrial biogenesis and prevents ROS production. *J Neurochem*. Mar. 2011; 116(6):1148-59. doi: 10.1111/j.1471-4159.2011.07171.x. Epub Jan. 28, 2011.

D'Antona G, Ragni M, Cardile A, Tedesco L, Dossena M, Bruttini F, Caliaro F, Corsetti G, Bottinelli R, Carruba MO, Valerio A, Nisoli E. Branched-chain amino acid supplementation promotes survival and supports cardiac and skeletal muscle mitochondrial biogenesis in middle-aged mice. *Cell Metab*. Oct. 6, 2010; 12(4):362-72.

Tedesco L, Valerio A, Dossena M, Cardile A, Ragni M, Pagano C, Pagotto U, Carruba MO, Vettor R, Nisoli E. Cannabinoid receptor stimulation impairs mitochondrial biogenesis in mouse white adipose tissue, muscle, and liver: the role of eNOS, p38 MAPK, and AMPK pathways. *Diabetes*. Nov. 2010; 59(11):2826-36. Epub Aug. 25, 2010.

Funicello M, et al., Cathepsin K null mice show reduced adiposity during the rapid accumulation of fat stores. *PLoS One*. Aug. 1, 2007; 2(1).

de Lange P, Feola A, Ragni M, Senese R, Moreno M, Lombardi A, Silvestri E, Amat R, Villarroya F, Goglia F, Lanni A. Differential 3,5,3'-triiodothyronine-mediated regulation of uncoupling protein 3 transcription: role of Fatty acids. *Endocrinology*. Aug. 2007; 148(8):4064-72.

de Lange P, Farina P, Moreno M, Ragni M, Lombardi A, Silvestri E, Burrone L, Lanni A, Goglia F. Sequential changes in the signal transduction responses of skeletal muscle following food deprivation *FASEB J*. Dec. 2006; 20(14):2579-81.

Silvestri E, de Lange P, Moreno M, Lombardi A, Ragni M, Feola A, Schiavo L, Goglia F, Lanni A Fenofibrate activates the biochemical pathways and the de novo expression of genes related to lipid handling and uncoupling protein-3 functions in liver of normal rats. *Biochim Biophys Acta*. May-Jun. 2006; 1757(5-6):486-95.

Lanni A, Moreno M, Lombardi A, de Lange P, Silvestri E, Ragni M, Farina P, Baccari GC, Fallahi P, Antonelli A, Goglia F. 3,5-diiodo-L-thyronine powerfully reduces adiposity in rats by increasing the burning of fats *FASEB J*. Sep. 2005; 19(11):1552-4. Epub Jul. 12, 2005.

Silvestri E, Moreno M, Lombardi A, Ragni M, de Lange P, Alexson SE, Lanni A, Goglia F Thyroid-hormone effects on putative biochemical pathways involved in UCP3 activation in rat skeletal muscle mitochondria. *FEBS Lett*. Mar. 14, 2005; 579(7):1639-45.

De Lange P., et al., Combined cDNA array/ RT-PCR analysis of the gene expression profile in rat gastrocnemius muscle: relation to its adaptive function in energy metabolism during fasting. *FASEB J*. Feb. 2004; 18(2):350-2.

Moreno M., et al., Lipid metabolism, and triiodothyronine in rat gastrocnemius muscle; interrelated roles of uncoupling protein 3, mitochondrial thioesterase, and coenzyme Q. *FASEB J*. Jun. 2003; 17(9):1112-4.

Albina et al., Temporal expression of different pathways of 1-arginine metabolism in healing wounds, *J Immunol* vol. 144, pp. 3877-3880, 1990.

Eming SA et al., Regulation of angiogenesis: Wound healing as a model, *Progress in Histochemistry and Cytochemistry*, vol. 42(3): 115-170, Dec. 10, 2007.

Frank et al., Induction of Inducible Nitric Oxide Synthase and its Coressponding Tetrahydrobiopterin-Cofactor-Synthesizing Enzyme GTP-Cyclohydrolase I During Cutaneous Wound Repair, The Society for Investigative Dermatology, Inc., *J Invest Dermatol* 111: 1058, 1998.

Ring BD et al., Systemically and Topically Administered Leptin Both Accelerate Wound Healing in Diabetic ob/ob Mice, *Endocrinology* vol. 141(1): 446-449, 2000.

Roberts et al., Transforming growth factor type β: Rapid induction of fibrosis and angiogenesis in vivo and stimulation of collagen formation in vitro, *Proc Nat Acad Sci* USA 83: 4167-4171, 1986.

Schwentker et al., Nitric oxide and wound repair: role of cytokines?, *Nitric Oxide* vol. 7, Issue 1, pp. 1-10, Aug. 2002.

Steed D.L., The Role of Growth Factors in Wound Healing, *Surgical Clinics of North America*, vol. 77, pp. 575-586, 1997.

Vodovotz et al., Mechanisms of Suppresison of Macrophage Nitric Oxide Release by Transforming Growth Factor β, *J Exp Med* 178: 605-613, 1993.

Witte, M.B. et al., Role of nitric oxide in wound repair, *Am J Surg*. vol. 183, pp. 406-412, 2002.

Yamasaki et al., Reversal of Impaired Wound Repair iniNOS-deficient Mice by Topical Adenoviral-mediated iNOS Gene Transfer, *J Clin Investigation, Inc*., vol. 101, No. 5,pp. 967, 1998.

Corsetti, G. et al., R. Topic application of dressing with amino acids improves cutaneous wound healing in aged rats, *Acta histochemica*, 2010, vol. 112, pp. 497-507.

Grose R, Martin P. Parallels between wound repair and morphogenesis in the embryo. *Semin Cell Dev Biol* 10: 395-404, 1999.

Harty M, et al., Regeneration or scarring: an immunologic perspective. *Dev Dyn* 226: 268-279, 2003.

Klyce S. Electrical profiles in the corneal epithelium. J Phisiol226: 407-429, 1972. Li DQ, Tseng SC. Three patterns of cytokine expression potentially involved in epithelialfibroblast interactions of human ocular surface. *J Cell Physiol* 163: 61-70, 1995.

Three patterns of cytokine expression potentially involved in epithelialfibroblast interactions of human ocular surface. *J Cell Physiol* 163: 61-70, 1995.

Lu L, Reinach PS, WY Kao. Corneal epithelium wound healing. *Exp Biol and Med* 226(7). 653-664, 2001.

Nishimura T, et al., Effects of hepatocyte growth factor, transforming growth factor-beta 1 and epidermal growth factor on bovine corneal epithelial cells under epithelial-keratinocyte interaction in reconstruction culture. *Exp Eye Res* 66: 105-116, 1998.

Veno M, et al., Accelerated wound healing of alkali-burned corneas in MRL mice is associated with a reduced inflammatory signature. *Invest Ophthalm & Visual Sci* 46 (11): 4097-4106, 2005.

Whitby DJ, et al., Rapid epithelisation of foetal wounds is associated with the early deposition of tenascin. *J Cell Sci* 99:586, 1991.

\* cited by examiner

WOUND-HEALING PHARMACEUTICAL COMPOSITIONS IN THE FORM OF A STERILE POWDER BASED ON AMINO ACIDS AND SODIUM HYALURONATE

CROSS REFERENCE TO RELATED APPLICATIONS

The present application is a continuation of U.S. patent application Ser. No. 12/091,551 filed on Apr. 25, 2008 and incorporated herein by reference in its entirety, which is the national stage entry of PCT/EP2006/009968 filed on Oct. 16, 2006 which, in turn, claims priority to Italian Patent Application MI2005A002037 filed on Oct. 26, 2005. The present application may also be related to U.S. patent application Ser. No. 12/091,462 filed on Apr. 24, 2008, and the related continuation application Ser. No. 12/954,840 filed on Nov. 26, 2010 and to U.S. patent application Ser. No. 12/091,481 filed on Apr. 24, 2008.

FIELD OF INVENTION

The present invention relates to wound-healing pharmaceutical compositions in the form of a sterile powder based on amino acids and sodium hyaluronate.

PRIOR ART

In the absence of suitable preventive actions, patients who are paralysed or bedridden for long periods are liable to ischaemic necrosis and ulceration of the tissues covering projecting bones, especially in the sacral, ischial, malleolar, heel and great trochanter regions.

Bedsores and chronic ulcerous wounds are usually treated with gentle massage to restore the circulation, possibly with mechanical removal of the necrotic tissue and cleansing with soap (which can cause oedema or dehydration), or with hydrophilic polymers, hydrogen peroxide or alcohol rubs (which can cause damage because the removal of the fats in the cutaneous tissue dries and cracks the skin).

Serious burns also require debridement of the affected area and removal of necrotic tissue.

DESCRIPTION OF THE INVENTION

It has now been found that the combination of some amino acids with sodium hyaluronate is particularly effective in promoting the process of cell reintegration which forms the basis for fast wound-healing, aiding the reconstruction of connective tissue and the consequent regeneration of epithelial cells.

The invention therefore relates to wound-healing pharmaceutical compositions in the form of a sterile powder, containing, as active ingredient, a combination of:
 a) glycine and proline;
 b) sodium hyaluronate; and possibly
 c) lysine and leucine.

More particularly, the compositions according to the invention contain glycine, L-proline and sodium hyaluronate, and possibly L-lysine in hydrochloride form, and L-leucine.

The compositions according to the invention have proved a surprising adjuvant effect in promoting the healing of wounds which cannot be stitched and have seriously damaged the dermis, including with loss of skin substance, such as chronic ulcerous wounds, serious burns and bedsores.

The compositions according to the invention promote the elimination of necrotic tissue, thus facilitating more rapid regeneration of the tissues, and maintain the ideal humidity conditions to aid re-epithelialisation of the skin lesions, at the same time preventing the spread of germs.

According to the invention, the powder compositions will take the form of two separate capsules, one containing only proline, and the other containing the remaining active ingredients.

Separation of proline from the other active ingredients in the powder form is necessary for reasons of stability, because under conditions of low humidity, the proline —$NH_2$ group reacts with the hydroxyl groups on the hyaluronate, giving rise to a Maillard reaction, which considerably darkens the powder due to degradation of the amino acids.

Powders from the two separate capsules will be applied to the affected area after removing any foreign material by thorough washing with a hydrogen peroxide solution or saline solution, and removing of any excess blood with sterile gauze.

The compositions according to the invention will contain the various active ingredients within the following percentage ranges by weight:
 glycine 0.5 to 2%;
 L-proline: 0.2 to 1.5%;
 sodium hyaluronate: 0.5 to 3%;
 and possibly
 L-lysine hydrochloride: 0.05 to 1%;
 L-leucine: 0.05 to 0.3%.

According to a preferred aspect, the compositions according to the invention will contain the various active ingredients in the following percentages by weight:
 glycine 1%;
 L-proline: 0.75%;
 sodium hyaluronate: 1.33%;
 and possibly
 L-lysine hydrochloride: 0.1%;
 L-leucine: 0.15%.

The compositions according to the invention can be formulated suitably for the topical administration in the form of a sterile powder, and prepared according to conventional methods well known in pharmaceutical technology, such as those described in Remington's Pharmaceutical Handbook, Mack Publishing Co., N.Y., USA, using excipients, solubilisers, emollients, stabilisers, emulsifiers, pH regulators, and preservatives acceptable for their final use.

Pharmacological Trial

The ability of the compositions of the invention to heal chronic sores in elderly patients, diabetics and patients with vascular disease was evaluated.

In particular, 40 elderly patients suffering from bedsores, 36 Type II diabetics with ulcers extending to the lower limbs, and 32 patients with post-phlebitic ulcers were evaluated.

The treatment was given three/four times a week, depending on the severity of the lesions, by spreading the sterile powder on the wound.

The bedsores had to have a de-epithelialised area of over 10 $cm^2$ which had already been treated by conventional means for over 4 months, without any evident results. The type of bandage was irrelevant.

The sore was clinically evaluated and photographed before treatment in the fourth and eighth weeks of the trial. "Healing" was defined as closing of the wounds, and "improvement" as a reduction in size of the treated area exceeding 70% of the initial area.

By the fourth week of treatment 18 patients showed an improvement, namely a reduction in size of the sore of over 70%, and 2 were completely healed; by the end of the observation period (8th week), 24 patients were healed, 10 had improved and 3 patients presented a reduction of under 50% in the de-epithelialised area. 2 Patients were hospitalized for concomitant pathologies and 1 worsened due to superinfection.

Of the 36 diabetics with ulcers of various areas and depths, which had already been treated unsuccessfully for at least four months prior to our study, 12 were healed after four weeks' treatment, and another 30 no longer presented ulcerated areas by the end of treatment period. In 4 particularly serious cases there was an improvement, but the sore was still present by the end of the 8th week of treatment.

In patients with post-phlebitic ulcers who had already undergone conventional treatment for at least two months with no result, the administration of the sterile powder compositions according to the invention led to healing within one month in 18 patients and by the end of treatment (8th week) in another 10 patients, making a total of 28 out of 32 treated.

In conclusion, in the case of bedsores, diabetic and post-phlebitic skin ulcers, the sterile powder compositions according to the invention obtained healing indexes (expressed as % improvement) exceeding 80% by comparison with conventional treatment.

An example of a sterile powder formulation according to the invention is set out below.

EXAMPLE

Each box contains five blister packs, each containing two hard gelatin capsules (capsule A and capsule B).

Each capsule contains 438 mg (capsule A) and 150 mg (capsule B) of sterile powder.

Before topical application, one capsule A and one capsule B are opened, and the powder contained in them is poured onto the wound.

The compositions of capsule A and capsule B are as follows:

Capsule A

Each Capsule A (format 000—Snap-Fit—Code: 23000), transparent bright pink, contains 438 mg of powder with the following composition:

| Ingredients Powder | One capsule contains (mg) |
| --- | --- |
| Sodium hyaluronate | 199.47 |
| Glycine | 182.10 |
| L-Lysine hydrochloride | 34.89 |
| L-Leucine | 21.54 |
| Total | 438.00 |

Capsule B

Each Capsule B (format 000—Snap-Fit—Code: 43000), transparent, contains 150 mg of powder with the following composition:

| Ingredients Powder | One capsule contains (mg) |
| --- | --- |
| L-Proline | 150.0 |
| Total | 150.0 |

The invention claimed is:

1. A topical pharmaceutical composition in sterile powder form, containing as active ingredient a combination of:
    a) glycine and L-proline; and
    b) sodium hyaluronate;
wherein glycine, L-proline and sodium hyaluronate are comprised within the following percentage ranges by weight:
    glycine 0.5 to 2%;
    L-proline: 0.2 to 1.5%; and
    sodium hyaluronate: 0.5 to 3%.

2. The topical pharmaceutical composition of claim 1, the composition further comprising as active ingredient:
    c) lysine hydrochloride and leucine.

3. The topical pharmaceutical composition of claim 2, wherein lysine hydrochloride is L-lysine hydrochloride, leucine is L-leucine and wherein L-lysine hydrochloride and L-leucine are comprised within the following percentage ranges by weight:
    L-lysine hydrochloride: 0.05 to 1%; and
    L-leucine: 0.05 to 0.3%.

4. The topical pharmaceutical composition of claim 1, wherein proline is L-proline, and wherein glycine, L-proline and sodium hyaluronate have the following percentage by weight:
    glycine 1%;
    L-proline: 0.75%; and
    sodium hyaluronate: 1.33%.

5. The topical pharmaceutical composition of claim 2, wherein lysine hydrochloride is L-lysine hydrochloride, leucine is L-leucine and wherein L-lysine hydrochloride and L-leucine have the following percentage by weight:
    L-lysine hydrochloride: 0.1%; and
    L-leucine: 0.15%.

6. A method for treating a wound in a biological tissue, the method comprising
    administering to the biological tissue a topical medicament in sterile powder, the topical medicament comprising the topical pharmaceutical composition of claim 1.

7. The method of claim 6, wherein the medicament further comprises as active ingredient
    c) lysine hydrochloride and leucine.

8. The method of claim 6, wherein the wound is a chronic ulcerous wound, a serious burn, a bedsore, or a surgical wound.

* * * * *